US00PP24797P2

(12) United States Plant Patent
van de Meer

(10) Patent No.: US PP24,797 P2
(45) Date of Patent: Aug. 19, 2014

(54) ***ASTILBE* PLANT NAMED 'RED QUIN'**

(50) Latin Name: ***Astilbe japonica*×*Astilbe arendsii***
Varietal Denomination: Red Quin

(71) Applicant: Hans van de Meer, Nieuwe Wetering (NL)

(72) Inventor: Hans van de Meer, Nieuwe Wetering (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 13/694,817

(22) Filed: Jan. 7, 2013

(51) Int. Cl.
*A01H 5/00* (2006.01)

(52) U.S. Cl.
USPC ..... Plt./407

(58) Field of Classification Search
USPC ..... Plt./407
See application file for complete search history.

*Primary Examiner* — Anne Grunberg
(74) *Attorney, Agent, or Firm* — C. A. Whealy

(57) ABSTRACT

A new and distinct cultivar of *Astilbe* plant named 'Red Quin', characterized by its tall, broadly upright and mounding plant habit; dark green-colored leaves; freely and uniformly flowering habit; red-colored flowers positioned above the foliar plane on strong dark red-colored peduncles; and good container and garden performance.

3 Drawing Sheets

Botanical designation: *Astilbe japonica*×*Astilbe arendsii*.
Cultivar denomination: 'RED QUIN'.

BACKGROUND OF THE INVENTION

The present invention relates to a new and distinct cultivar of *Astilbe*, botanically known as *Astilbe japonica*×*Astilbe arendsii* and hereinafter referred to by the name 'Red Quin'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from a cross-pollination made by the Inventor in 2006 in Nieuwe Wetering, The Netherlands, of an unnamed selection of *Astilbe japonica*, not patented, as the female, or seed, parent with an unnamed selection of *Astilbe arendsii*, not patented, as the male, or pollen, parent. The new *Astilbe* plant was discovered and selected by the Inventor as a single flowering plant from within the progeny of the stated cross-pollination in a controlled greenhouse environment in Nieuwe Wetering, The Netherlands in 2008.

Asexual reproduction of the new *Astilbe* plant by vegetative divisions in a controlled environment in Nieuwe Wetering, The Netherlands since 2008 has shown that the unique features of this new *Astilbe* plant are stable and reproduced true to type in successive generations.

SUMMARY OF THE INVENTION

Plants of the new *Astilbe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Red Quin'. These characteristics in combination distinguish 'Red Quin' as a new and distinct *Astilbe* plant:

1. Tall, broadly upright and mounding plant habit.
2. Dark green-colored leaves.
3. Freely and uniformly flowering habit.
4. Red-colored flowers positioned above the foliar plane on strong dark red-colored peduncles.
5. Good container and garden performance.

Plants of the new *Astilbe* differ primarily from plants of the parent selections in the following characteristics:

1. Plants of the new *Astilbe* are more vigorous than plants of the parent selections.
2. Plants of the new *Astilbe* have taller and stronger flowering stems than plants of the parent selections.
3. Plants of the new *Astilbe* are more freely-flowering than plants of the parent selections.
4. Plants of the new *Astilbe* have larger inflorescences than plants of the parent selections.

Plants of the new *Astilbe* can be compared to plants of *Astilbe arendsii* 'Glut', not patented. In side-by-side comparisons conducted in Nieuwe Wetering, The Netherlands, plants of the new *Astilbe* and 'Glut' differed in the following characteristics:

1. Plants of the new *Astilbe* were taller than plants of 'Glut'.
2. Plants of the new *Astilbe* had darker-colored leaves than plants of 'Glut'.
3. Plants of the new *Astilbe* were more freely flowering than plants of 'Glut'.
4. Plants of the new *Astilbe* had stronger flowering stems than plants of 'Glut'.
5. Plants of the new *Astilbe* had larger flowers than plants of 'Glut'.
6. Plants of the new *Astilbe* and 'Glut' differed slightly in flower color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of typical flowering plants of 'Red Quin' grown in containers in an outdoor nursery.

The photograph on the second sheet is a close-up view of typical developing inflorescences of 'Red Quin'.

The photograph on the third sheet is a close-up view of fully developed inflorescences of 'Red Quin'.

DETAILED BOTANICAL DESCRIPTION

The aforementioned photographs and following observations, measurements and values describe plants grown in four-liter containers during the late summer/early autumn in an outdoor nursery in Nieuwe Wetering, The Netherlands and under cultural practices typical of commercial *Astilbe* production. During the production of the plants, day temperatures ranged from 14° C. to 30° C. and night temperatures ranged from 6° C. to 16° C. Plants were 18 months old when the photographs and description were taken. In the following description, color references are made to The Royal Horticultural Society Colour Chart, 2007 Edition, except where general terms of ordinary dictionary significance are used.

Botanical classification: *Astilbe japonica*×*Astilbe arendsii* 'Red Quin'.

Parentage:

- *Female, or seed, parent*.—Unnamed *Astilbe japonica* seedling selection, not patented.
- *Male, or pollen, parent*.—Unnamed *Astilbe arendsii* seedling selection, not patented.

Propagation:

- *Type*.—By divisions.
- *Time to initiate roots*.—About three weeks at temperatures about 20° C.
- *Root description*.—Thick, fleshy; brown and white in color.
- *Rooting habit*.—Freely branching; dense.

Plant description:

- *Plant form and growth habit*.—Herbaceous perennial; tall, broadly upright and mounding plant form with inflorescences held above the foliar plane; flowering stems and leaves basal; freely flowering with numerous basal branches developing per plant; moderately vigorous to vigorous growth habit; freely and uniformly flowering habit.
- *Growth rate*.—Moderate to rapid; from divisions, about ten months are required to produce fully-grown flowering plants in containers.
- *Plant height* (*soil level to top of foliar plane*).—About 63 cm.
- *Plant height* (*soil level to top of inflorescences*).—About 86.7 cm.
- *Plant width* (*spread*).—About 77 cm.
- *Stem description*.—Length: About 55 cm. Diameter: About 4 mm. Strength: Strong, sturdy. Texture: Sparsely pubescent. Color: Close to 146C.

Foliage description:

- *Arrangement*.—Alternate in basal rosettes; biternately compound; about 25 leaflets per leaf.
- *Leaf length* (*excluding petiole*).—About 29.9 cm.
- *Leaf width*.—About 28.8 cm.
- *Terminal leaflet length*.—About 5.6 cm.
- *Terminal leaflet width*.—About 3.2 cm.
- *Lateral leaflet length*.—About 5.2 cm.
- *Lateral leaflet width*.—About 2.8 cm.
- *Leaf shape*.—Roughly deltoid to broadly ovate in outline.
- *Lateral and terminal leaflet shape*.—Elliptic to ovate.
- *Lateral and terminal leaflet apex*.—Apiculate.
- *Lateral and terminal leaflet base*.—Attenuate.
- *Lateral and terminal leaflet margin*.—Biserrate.
- *Lateral and terminal leaflet texture, upper and lower surfaces*.—Moderately pubescent; slightly rough.
- *Lateral and terminal leaflet venation pattern*.—Pinnate.
- *Lateral and terminal leaflet color*.—Developing leaflets, upper surface: Close to 144A. Developing leaflets, lower surface: Close to 143C. Fully expanded leaflets, upper surface: Close to N137A to N137B; venation, close to 144B. Fully expanded leaflets, lower surface: Close to 147B; venation, close to 146D.
- *Leaf petiole length*.—About 25.9 cm.
- *Leaf petiole diameter*.—About 3 mm.
- *Leaflet petiole length*.—About 7 mm.
- *Leaflet petiole width*.—About 1 mm.
- *Leaf and leaflet petiole texture, upper and lower surfaces*.—Sparsely pubescent.
- *Leaf and leaflet petiole color, upper and lower surfaces*.—Close to 144A to 144B.

Flower description:

- *Flower type and flowering habit*.—Single rotate flowers arrange on terminal panicles; flowers face upright, outwardly or drooping depending on position on the inflorescence; racemes roughly conical in shape; freely and uniformly flowering habit with about 1,250 flowers per inflorescence.
- *Fragrance*.—Moderately strong; sweet, pleasant.
- *Natural flowering season*.—Plants begin flowering about ten months after planting; continuously flowering from early to late summer in The Netherlands.
- *Postproduction longevity*.—Flowers last about ten days on the plant; flowers persistent.
- *Flower buds*.—Height: About 3 mm. Diameter: About 1.5 mm. Shape: Broadly ovoid. Color: Close to 60B.
- *Inflorescence height*.—About 25.6 cm.
- *Inflorescence diameter*.—About 13.7 cm.
- *Flower diameter*.—About 1.1 cm.
- *Flower depth*.—About 7 mm.
- *Petals*.—Quantity per flower: Typically five in a single whorl. Length: About 6 mm. Lobe width: About 1 mm. Shape: Oblanceolate. Apex: Broadly acute. Margin: Entire. Texture, upper and lower surfaces: Smooth, glabrous. Color: Developing petals, upper and lower surfaces: Close to 60C. Fully expanded petals, upper and lower surfaces: Close to 60D; color becoming closer to 61A with development.
- *Sepals*.—Quantity per flower: Typically five in a single whorl, fused towards the base; campanulate-shaped calyx. Length: About 2.5 mm. Width: About 1 mm. Shape: Ovate. Apex: Acute. Margin: Entire. Texture, upper and lower surfaces: Smooth, glabrous. Color: Developing sepals, upper and lower surfaces: Close to 53B; towards the base, close to 56C. Fully expanded sepals, upper and lower surfaces: Close to 53C; towards the base, close to 56C.

*Peduncles*.—Length: About 24.8 cm. Diameter: About 2.5 mm. Angle: Erect to about 50° from vertical. Strength: Strong. Texture: Smooth, glabrous. Color: Close to 53A to 53C.

*Pedicels*.—Length: About 1 mm. Diameter: About 0.5 mm. Angle: About 50° from peduncle axis. Strength: Moderately strong. Texture: Smooth, glabrous. Color: Close to 181B.

*Reproductive organs*.—Stamens: Quantity per flower: Typically ten. Filament length: About 3 mm. Filament color: Close to 62C. Anther shape: Ovate, basifixed. Anther length: About 0.2 mm. Anther color: Close to 63C to 63D. Pollen amount: Medium to abundant. Pollen color: Close to 156D. Pistils: Quantity per flower: Typically two. Pistil length: About 1.5 mm. Stigma shape: Club-shaped. Stigma color: Close to 60C. Style length: About 1.3 mm. Style color: Close to 60D. Ovary color: Close to 61C to 61D.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Red Quin' as illustrated and described.

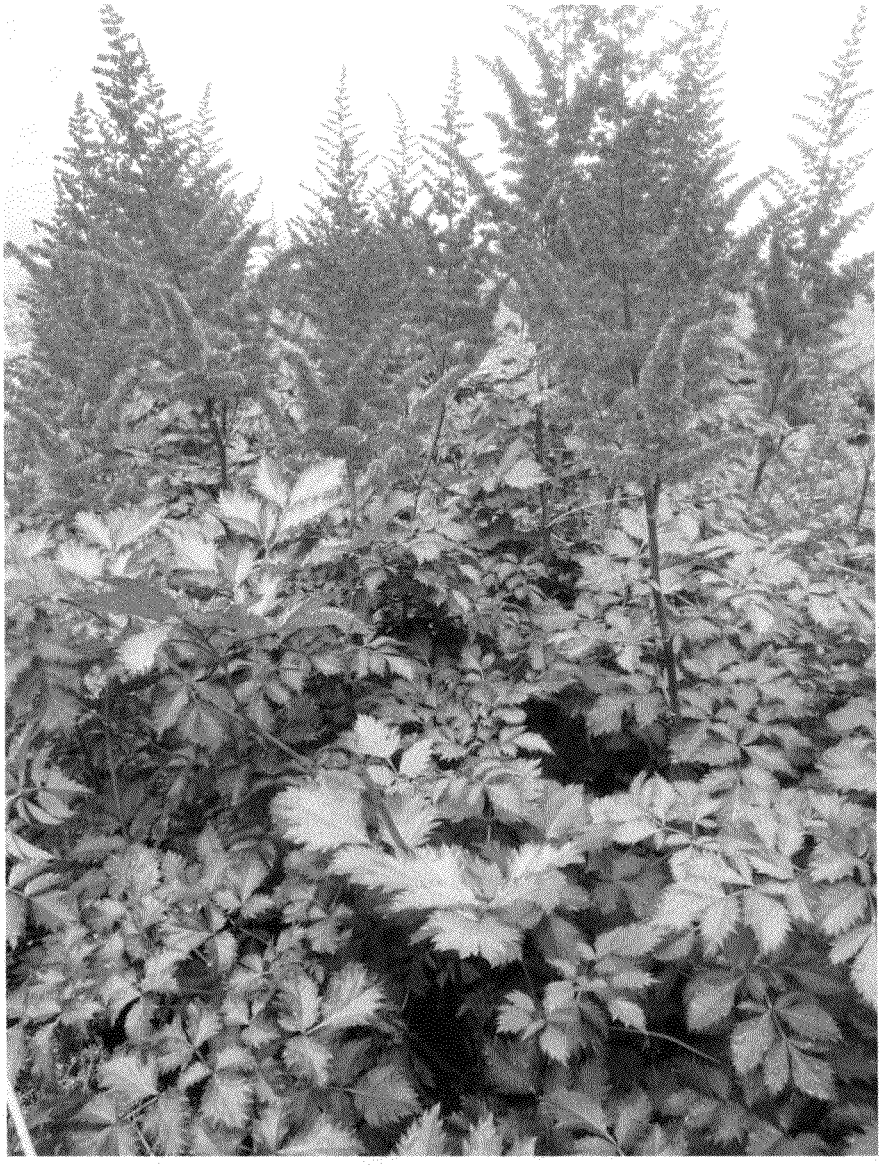

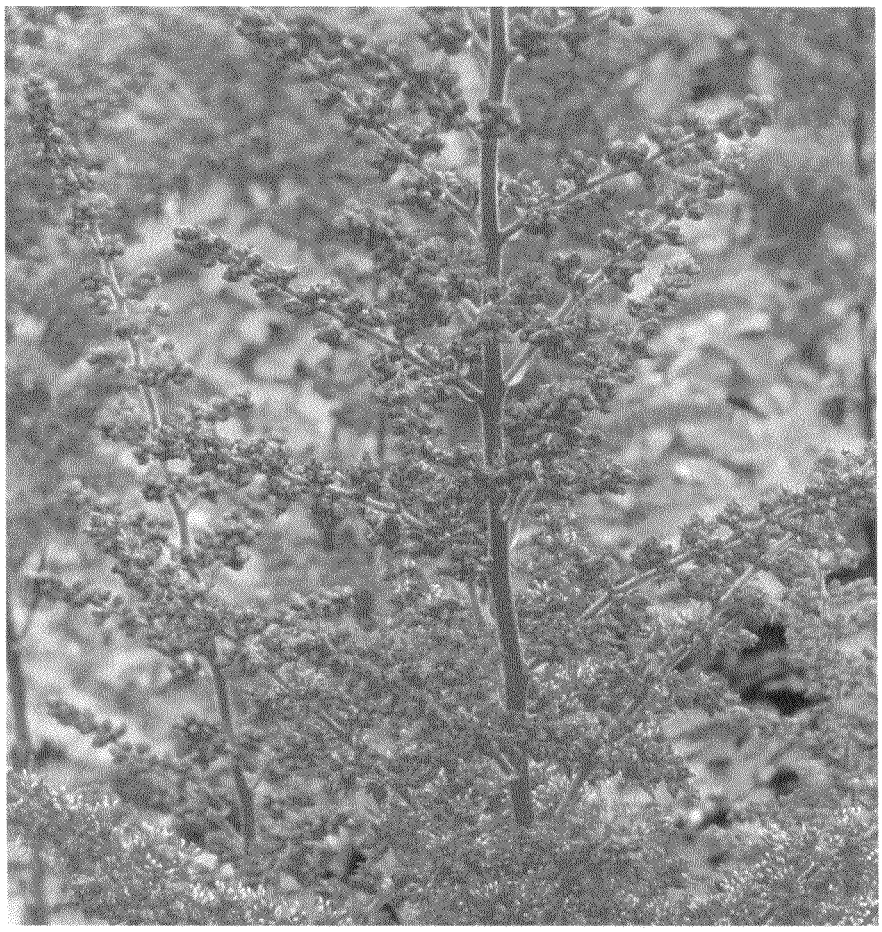

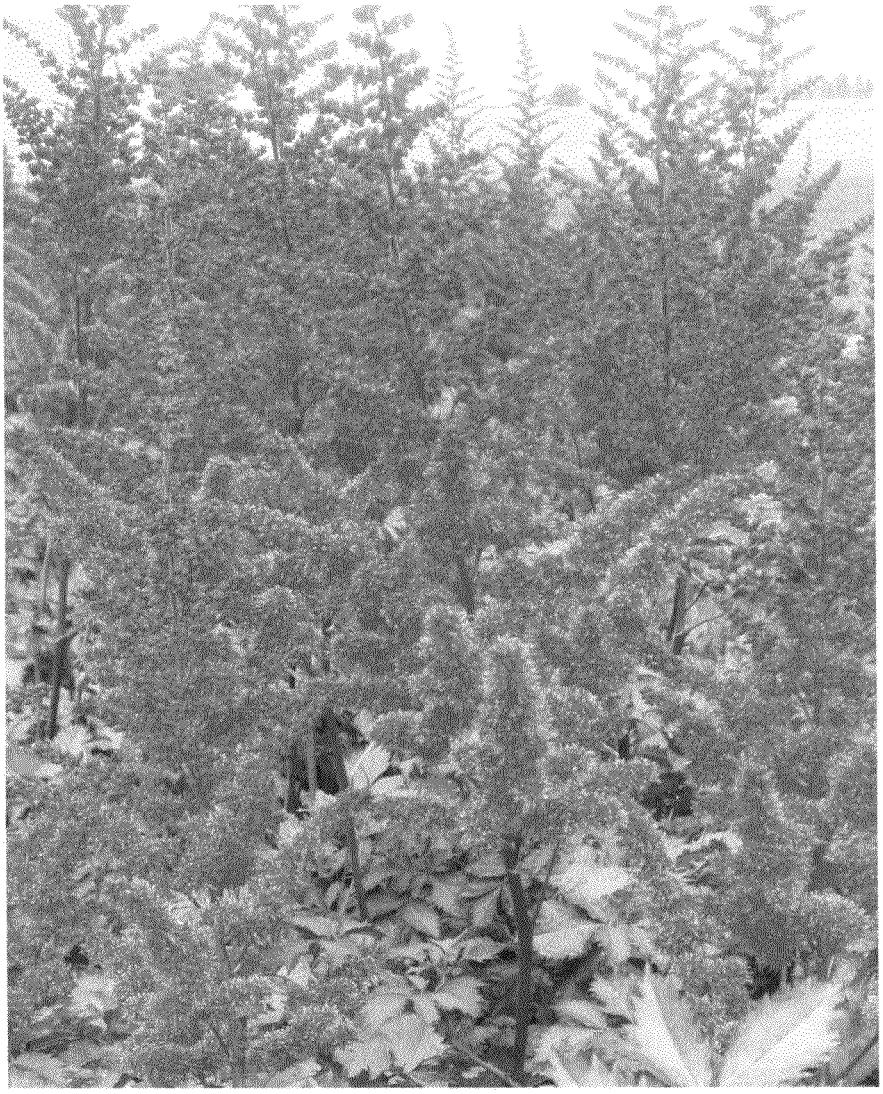

* * * * *